United States Patent [19]

Cottman et al.

[11] Patent Number: 5,093,517
[45] Date of Patent: Mar. 3, 1992

[54] METHOD FOR THE ESTERIFICATION OF THIOPROPIONATES

[75] Inventors: Kirkwood S. Cottman, Akron; Joseph A. Kuczkowski, Munroe Falls, both of Ohio

[73] Assignee: The Goodyear Tire & Rubber Company, Akron, Ohio

[21] Appl. No.: 23,735

[22] Filed: Mar. 9, 1987

[51] Int. Cl.$^5$ .............. C07C 323/62; C07C 323/56; C07C 323/52; C07C 319/20

[52] U.S. Cl. .................. 560/152; 560/15; 560/92; 560/100; 560/103; 560/105; 560/112; 560/125; 560/145; 560/234

[58] Field of Search .............. 560/125, 145, 152, 105, 560/103, 100, 112, 15, 234, 92

[56] References Cited

U.S. PATENT DOCUMENTS

| | | | |
|---|---|---|---|
| 2,720,507 | 10/1955 | Caldwell | 560/92 |
| 3,758,549 | 9/1973 | Dexter | 560/152 |
| 4,301,296 | 11/1981 | Kuczkowski | 560/152 |

Primary Examiner—Vivian Garner
Attorney, Agent, or Firm—Bruce J. Hendricks

[57] ABSTRACT

There is disclosed a method for making compounds such as 3,6,9-trioxaundecane-1,11-bis (3-n-dodecylthiopropionate) which comprises reacting an alkyl thiopropionate with a glycol at temperatures between 50° C. and 180° C. in the presence of a catalytic amount of a dialkyl tin oxide.

8 Claims, No Drawings

METHOD FOR THE ESTERIFICATION OF THIOPROPIONATES

TECHNICAL FIELD

This invention is concerned with a process for the manufacture of a rubber chemical that has demonstrated superior activity as a synergist with amine and phenolic antioxidants in the stabilization of styrene butadiene rubbers and nitrile butadiene-type rubbers. The instant invention provides a method for the preparation of compounds such as 3,6,9-trioxaundecane-1,11-bis(3-n-dodecylthiopropionate) which avoids the prior art problems of objectionable odor and expensive and time consuming deorderizing process such as nitrogen stripping. Through the discovery of the instant invention, tin catalysts such as dibutyl tin oxide, produce the desired materials without a foul odor and eliminates the need for product deorderization. In addition, the catalyst for the instant invention allows for the rapid production of the material in high purity.

BACKGROUND ART

This invention relates to a method to produce a chemical that has demonstrated activity in the stabilization of elastomeric polymers.

The compounds produced by the process of this invention exhibit synergistic activity with known amine and phenolic antidegradants and the combination provides a long lasting and persistent antioxidative protection to elastomeric polymers.

U.S. Pat. Nos. 4,241,217, 4,301,298 and 4,125,515 disclose combinations of esters and amines wherein an ester such as 3,6,9-trioxaundecane-1,11-bis(3-n-dodecyl-thiopropionate) is combined with conventional amine antioxidants (such as N,N'-diphenyl-para-phenylenediamine or polymer bound antidegradants such as N-(4-anilinophenyl)methacrylamide) to produce improved antioxidant systems for elastomeric-type polymers. A process for the preparation of the esters is also illustrated in U.S. Pat. Nos. 3,629,194 and 3,758,549.

U.S. Pat. No. 4,216,116 discloses a combination of a phenolic antioxidant with an ester such as 3,6,9-trioxaundecamethylene bis[3-(dodecylthio)propionate to stabilize polymers against oxidative degradation.

These esters or synergists are conventionally prepared by reacting a suitable thiol with an ester of acrylic or methacrylic acid in the presence of a basic catalyst such as KOH or benzyl trimethyl ammonium hydroxide. These synergists have also been prepared by reacting a suitable acid with an alcohol in a known acid catalyzed esterification procedure as described in U.S. Pat. No. 2,601,063.

A previously used process to prepare these synergists involves the initial reaction of a suitable thiol with a lower alkyl ester of acrylic or methacrylic acid. The alkylthiopropionate ester is then esterified with a high molecular weight glycol.

U.K. Patent 1,047,389 describes a process for the manufacture of dialkyl tin oxides and hydroxides. The dialkyl tin oxides are useful as intermediates in the preparation of PVC stabilizers, bacteriocides, fungicides and molluscicides. This British patent describes a process for the preparation of alkyl tin oxides which comprises reacting tin with an alkyl or alkenyl halide in the presence of a catalyst and an organic compound which is a Lewis base.

U.S. Pat. No. 2,720,507 describes the use of an organometallic tin catalyst for the preparation of polyesters. This patent discloses tin compounds, such as dialkyl tin oxides, as a condensing agent in the preparation of high melting linear polyesters. This patent describes a process wherein carboxylic acids are esterified by reaction with esters in the presence of a catalytic amount of a tin halide catalyst, the reaction being effected at temperatures ranging from 0° C. to about 150° C.

U.S. Pat. No. 4,206,143 discloses a method for making N-substituted acrylamide or N-substituted methacrylamides which comprises reacting an alkyl ester of acrylic acid or of methacrylic acid with an aliphatic amine or with an aromatic amine at a temperature between 50° C. and 180° C. in the presence of a catalytic amount of a dialkyl tin oxide.

U.S. Pat. No. 4,492,801 describes a one-step process for the preparation of N-substituted (meth)acrylamides from the reaction of a (meth)acrylate ester and an amine over a catalytic amount of a metal alkoxide catalyst. These catalysts, such as stannous dimethoxide, provide high selectivity to the N-substituted (meth)acrylamides and little selectivity to the Michael addition adduct which would predominate in the absence of these catalysts.

None of the prior art discloses or suggests that dialkyl tin oxides can be used to enhance the reaction between an alkyl thiopropionate and a glycol to produce compounds such as 3,6,9-trioxaundecane-1,11-bis(3-n-dodecylthiopropionate).

DISCLOSURE OF THE INVENTION

There is disclosed the process for the preparation of a compound of the following structural formula:

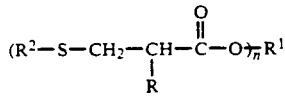

wherein n is an integer from 1 to 4 and R is hydrogen or methyl; when n is 1, $R^1$ is selected from the group consisting of alkyl radicals having 1 to 18 carbon atoms, aryl radicals having 6 to 12 carbon atoms, aralkyl radicals having 7 to 12 carbon atoms and cycloalkyl radicals having 5 to 12 carbon atoms; when n is 2, $R^1$ is selected from the group consisting of alkylene radicals having 2 to 18 carbon atoms, cycloalkylene radicals having 5 to 12 carbon atoms, arylene radicals having 6 to 12 carbon atoms, a radical of the structure:

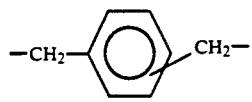

polyalkyl glycol ether radicals having the structure:

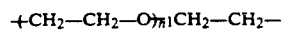

wherein $n^1$ is an integer from 1 to 7; thioether radicals having the structure:

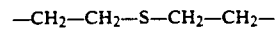

when n is 3 or 4, $R^1$ is an aliphatic hydrocarbon radical having the formula $C_yH_{2y+2-n}$, wherein y is an integer from 3 to 6;

$R^2$ is selected from the group consisting of alkyl radicals having 1 to 24 carbon atoms (preferably primary alkyl), aryl radicals having 6 to 12 carbon atoms and aralkyl radicals having 7 to 12 carbon atoms;

said process comprises reacting an alkyl thiopropionate of the structural formula:

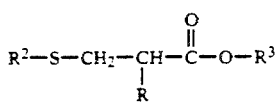

wherein $R^3$ is methyl or ethyl and $R^2$ and R are described above: with a glycol at temperatures between 50° C. and 180° C. in the presence of a catalytic amount of a dialkyl tin oxide.

The synergists that can be prepared in accordance with the process of this invention are illustrated by the following compounds:

3,6,9-trioxaundecane-1,11-bis(3-n-dodecylthiopropionate);
3,6-dioxaoctane-1,8-bis(3-n-dodecylthiopropionate);
3,6,9-trioxaundecane-1,11-bis(3-n-dodecylthio-2-methylproprionate);
3-oxapentane-1,5-bis(3-n-dodecyl-thiopropionate).

Other esters illustrating the esters of the present invention are as follows:
phenyl-(3-phenylthiopropionate);
phenyl-1,4-bis-(3-t-dodecylthiopropionate);
naphthyl-1-(3-n-dodecylthiopropionate);
naphthyl-2-(3-n-octyl-2-methylpropionate);
naphthyl-1,4-bis-(3-n-hexylthiopropionate);
phenyl-(3-n-dodecylthio-2-methylpropionate);
benzyl-(3-t-dodecylthiopropionate);
benzyl-(3-n-dodecylthio-2-methylpropionate);
p-xylyl-alpha,alpha'-bis(3-n-octyl-2-methylpropionate);
o-xylyl-alpha,alpha'-bis(3-n-dodecylthiopropionate);
ethane-1,2-bis(3-n-dodecylthiopropionate);
ethane-1,2-bis(3-t-dodecylthiopropionate);
butane-1,4-bis(3-benzylthioproprionate);
pentane-1,5-bis(3-n-hexylthio-2-methylproprionate);
propane-1,2-bis(3-n-dodecylthiopropionate);
octane-1,8-bis(3-n-tetracosylthiopropionate);
3,6,9-trioxaundecane-1,11-bis(3-phenylthiopropionate);
3,6,9-trioxaundecane-1,11-bis(3-benzylthio-2-methylpropionate);
3-oxapentane-1,5-bis(3,benzylthio-2-methylpropionate);
3-thiapentane-1,5-bis(n-octylthio-2-methylpropionate);
3-thiapentane-1,5-bis(benzylthio-2-methylpropionate);
1,1,1-trimethanolpropane-tris(3-n-octylthiopropionate);
1,1,1-trimethanolpropane-bis(3-t-dodecylthiopropionate);
pentaerythritol-tetrakis-(3-phenylthiopropionate);
pentaerythritol-tetrakis-(3-n-dodecylthio-2-methylpropionate).

The alkyl thiopropionate starting material can be prepared by reacting a suitable thiol with an ester of acrylic or methacrylic acid in the presence of a basic catalyst such as potassium hydroxide or benzyl trimethyl ammonia hydroxide. The alkyl thiopropionate can also be prepared by reacting a suitable acid with an alcohol in a simple acid catalyzed esterification procedure such as described in U.S. Pat. No. 2,601,063.

The process of the instant invention is specifically applicable to the preparation of the synergists which is preceded by an initial reaction of a suitable thiol with a lower alkyl ester of acrylic or methacrylic acid. The alkyl thiopropionate ester is then reacted with a high molecular weight glycol. Heretofore, the commercial production of such synergists was through a two-stage reaction process wherein toluene sulfonic acid was used as the second-stage catalyst. The synergists produced through the use of toluene sulfonic acid (TSA) have a foul objectionable odor. The odor causing components had to be removed by an expensive and time consuming nitrogen stripping process. Such equipment for the removal of the objectionable odor causing components is both expensive and energy intensive. In addition, the previously TSA catalyzed reactions took from 5 to 10 hours to produce only a 50 to 75% pure product. The present invention overcomes the numerous shortcomings of the prior art methodology through the discovery that a tin catalyst, such as dibutyl tin oxide (DBTO), can be used to accelerate the reaction between the thiopropionate and the glycol, and it was unexpectedly discovered that the DBTO catalyzed reactions are complete in as little as a half an hour and that the products are as high as 90% pure. The most beneficial aspect of the instant invention resides in the discovery that the use of dialkyl tin oxides, in the process described, will not produce by-products which have a foul and objectionable odor. Thus the requirement of nitrogen stripping is alleviated.

The prior use of a highly acidic catalyst such as toluene sulfonic acid appears to promote the formation of odor causing components. Whereas, the use of a dialkyl tin oxide does not promote the formation of the odor causing components.

In the process of the invention commercially available dialkyl tin oxides are useful and dibutyl tin oxide is preferably used as the catalyst. However, other dialkyl tin oxides are suitable. They can, for example, contain from 1 to 12 carbon atoms in each alkyl group. The catalyst can be added in an amount from 0.01 to 10% based on total weight of the reactants. In general, amounts from 0.05 to 2% give the most advantageous results. Dialkyl tin oxides in which each alkyl group has 4 to 8 carbon atoms are preferred.

Generally, one molar amount of the alkyl thioproprionate is reacted with one molar amount of contained hydroxyl groups in the glycol to form the desired end product. Typically, the propionate is combined with the glycol in the presence of a catalyst and the reaction mixture is heated. It is suitable to carry out the reaction at atmospheric pressure or reduced pressure and at or above the boiling point of the cleaved alcohol so that it can be removed from the reaction mixture.

The reaction temperature is usually between about 50° C. and 180° C. Preferably between 120°-150° C. However, higher temperatures encourage the formation of undesired polymers and by-products.

The crude product can be used directly in combination with antioxidants; however, a purification by recrystallization or distillation can be performed.

A better understanding of the present invention and many of its advantages will be realized by referring to the following specific examples given by way of illustration.

Best Mode for Carrying Out the Invention

As discussed previously, a first stage reaction product is reacted with a glycol in the presence of a dialkyl tin oxide to yield the synergist. The whole reaction scheme is shown below.

EXPERIMENT 2

First Stage

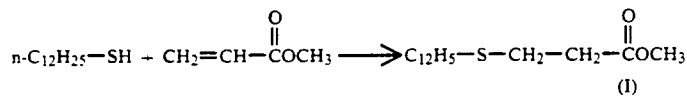

(I)

Second Stage-Process of the Invention

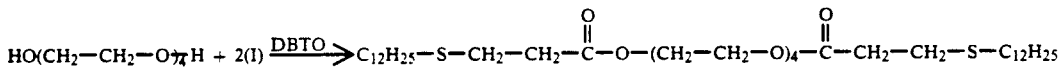

For experiments 1 through 4 and the controls the first stage reaction product was used without purification.

EXPERIMENT 1

Into a 3-neck flask equipped with a thermometer condenser and vacuum line was weighed 100 grams of 1st stage product, 33.4 grams of tetraethylene glycol The reactor was charged with 100 grams of 1st stage product, 33.4 grams of tetraethylene glycol and 0.5 grams of DBTO. The reactants were reacted at 140° C. for 3.8 hours while pulling a full vacuum through a dry ice trap. The dry ice trap volatiles weighed 11.26 grams. The GPC data below indicates that a 89.0% pure product formed after 3.8 hours.

TABLE II

| | GPC Data for a Product Which Was Catalyzed With 0.375 Weight % of DBTO | | | | | | | |
|---|---|---|---|---|---|---|---|---|
| Hours Reacted at 140° C. | * | 0 Hr | 0.5 Hr | 1.0 Hr | 1.5 Hr | 2.0 Hr | 3.0 Hr | 3.8 Hr. |
| 2:1 Main Component | N.D. | 21.8% | 71.0% | 76.7% | 81.9% | 82.4% | 85.6% | 89.0% |
| $C_{12}H_{25}-S-(CH_2)_2-\overset{O}{\underset{\|}{C}}-O(CH_2-CH_2-O)_{\overline{4}}H$ | 0.40% | 31.3% | 17.1% | 15.0% | 12.3% | 11.4% | 9.5% | 4.1% |
| 1st Stage Product | 73.7% | 41.0% | 11.3% | 8.0% | 6.7% | 6.1% | 4.8% | 4.1% |
| Tetraethylene Glycol | 25.8% | 5.8% | 0.57% | 0.25% | 0.15% | 0.08% | 0.07% | N.D. |

*Sample taken before heating to 140° C.

and 1.0 gram of dibutyl tin oxide (DBTO). The mixture was heated to 140° C. and a partial vacuum was pulled on the reactor through a dry ice trap to collect the by-product methanol. Samples of the reaction mixture were taken every 30 minutes and the reaction was stopped after 4.5 hours. The dry ice trap contained 11 grams of volatiles. The Gel Permeation Chromatography (GPC) data in Table I indicates that a 86.15 pure product formed at the end of 4.5 hours of reaction.

EXPERIMENT 3

The reactor was charged with 100 grams of 1st stage product, 33.4 grams of tetraethylene glycol and 0.1 grams of DBTO. The reactants were reacted at 140° C. for 4.5 hours while pulling a full vacuum through a dry ice trap. The GPC data below in Table III show that a 80.5% pure product formed.

TABLE I

| | GPC Data for a Product Which Was Catalyzed With 0.75 Weight % of DBTO | | | | | |
|---|---|---|---|---|---|---|
| Hours Reacted at 140° C. | .5 Hr. | 1.0 Hr. | 1.5 Hrs. | 2.0 Hrs. | 3.0 Hrs. | 4.5 Hrs. |
| 2:1 Main Component | 55.1% | 70.1% | 76.7% | 82.2% | 85.9% | 86.2% |
| $C_{12}H_{25}S-CH_2-CH_2-\overset{O}{\underset{\|}{C}}O(CH_2-CH_2O)_{\overline{4}}H$ | 24.4% | 17.2% | 13.5% | 10.9% | 8.8% | 9.2% |
| Unknown | .4% | Trace | 1.1% | .6% | .3% | .6% |
| 1st Stage Product | 18.6% | 12.8% | 8.2% | 6.2% | 5.0% | 4.0% |
| Tetraethylene Glycol | 1.6% | .7% | .3% | Trace | — | — |
| Methanol | Trace | Trace | .3% | Trace | — | — |

TABLE III

| | GPC Data for a Product Which Was Catalyzed With 0.075 Weight % of DBTO | | | | | | | |
|---|---|---|---|---|---|---|---|---|
| Hours Reacted at 140° C. | * | 0.0 Hr | 0.5 Hr | 1.0 Hr | 1.5 Hr | 2.0 Hr | 3.0 Hr | 4.0 Hr | 4.5 Hr |
| 2:1 Main Component | N.D. | .45% | 49.5% | 64.5% | 67.8% | 71.7% | 75.9% | 79.5% | 80.5% |
| $C_{12}H_{25}-S-CH_2-CH_2-\overset{O}{\underset{\|}{C}}O(CH_2-CH_2O)_4H$ | .40% | 7.5% | 26.5% | 20.6% | 19.3% | 17.5% | 15.4% | 12.7% | 12.5% |

TABLE III-continued

| | GPC Data for a Product Which Was Catalyzed With 0.075 Weight % of DBTO | | | | | | | | |
|---|---|---|---|---|---|---|---|---|---|
| Hours Reacted at 140° C. | * | 0.0 Hr | 0.5 Hr | 1.0 Hr | 1.5 Hr | 2.0 Hr | 3.0 Hr | 4.0 Hr | 4.5 Hr |
| 1st Stage Product | 73.7% | 89.0% | 21.8% | 13.7% | 12.2% | 10.4% | 8.8% | 7.5% | 6.9% |
| Tetraethylene Glycol | 25.8% | 4.9% | 1.8% | 0.9% | 0.6% | 0.4% | 0.2% | .08% | Trace |

*Sample taken before heating to 140° C

EXPERIMENT 4

The reactor was charged with 100 grams of 1st stage product, 33.4 grams of tetraethylene glycol, and 0.58 grams of toluene-sulfonic acid. The reactants were heated to 140° C. and reacted for 5 hours while pulling a full vacuum through a dry ice trap. The dry ice trap volatiles weighed 10.5 grams. The GPC data in Table 4 show that 76.9% pure product was formed.

TABLE IV

| | GPC Data for a Product Which Was Catalyzed With 0.43 Weight % of TSA | | | | |
|---|---|---|---|---|---|
| Hours Reacted at 140° C. | * | 0.0 Hrs. | 1.0 Hrs. | 2.0 Hrs. | 5.0 Hrs. |
| 2:1 Main Component | N.D. | 3.7% | 37.1% | 55.4% | 76.9% |
| $C_{12}H_{25}-S-CH_2-CH_2-\overset{O}{\underset{\|}{C}}O-(CH_2-CH_2-O)_4H$ | .4% | 13.7% | 28.3% | 20.9% | 12.8% |
| 1st Stage Product | 73.7% | 60.5% | 30.0% | 17.7% | 6.5% |
| Tetraethylene Glycol | 25.8% | 19.6% | 6.3% | 4.9% | 3.1% |

*Sample taken before heating to 140° C

Controls

The reactor described above was charged with 100 grams of the 1st stage product and 33.4 grams of tetraethyleneglycol. No catalyst was added to the reactor. The reactants were heated to 140° C. and allowed to react for five hours while pulling a full vacuum on the reactor. The product did not crystallize after being cooled to room temperature. This indicated that the 2nd stage reaction will not proceed without a catalyst.

The data from the examples amply demonstrates that a 62 to 77% pure product is obtained in one hour if dialkyl tin oxide is used as a catalyst. As previously noted, it takes as long as three and a half hours to produce a 62% pure product and more than five hours to produce a 72% pure product when the prior art toluene sulfonic acid is used in preparing the reaction product.

Industrial Applicability

The use of the process of the instant invention produces the unexpected benefits of reducing the undesirable, objectionable by-products which possess a foul odor and reduced reaction times that are at least one-half of that required with the prior art toluene sulfonic acid. Further, the instant process unexpectedly produces a nearly 90% pure product. The commercial advantages of the instant invention would be readily apparent to those skilled in the art.

What is claimed is:

1. A process for the preparation of a compound of the following structural formula:

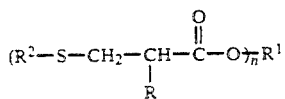

wherein n is an integer from 1 to 4, and R is hydrogen or methyl; when n is 1, $R^1$ is selected from the group consisting of alkyl radicals having 1 to 18 carbon atoms, aryl radicals having 6 to 12 carbon atoms, aralkyl radicals having 7 to 12 carbon atoms and cycloalkyl radicals having 5 to 12 carbon atoms; when n is 2, $R^1$ is selected from the group consisting of alkylene radicals having 2 to 18 carbon atoms, cycloalkylene radicals having 5 to 12 carbon atoms, arylene radicals having 6 to 12 carbon atoms, a radical of the structure:

polyalkyl glycol ether radicals having the structure
$-(CH_2-CH_2-O)_{n^1}CH_2-CH_2-$ wherein $n^1$ is an integer from 1 to 7; thioether radical having the structure:

$-CH_2-CH_2-S-CH_2-CH_2-$ when n is 3 or 4, $R^1$ is an aliphatic hydrocarbon radical having the formula $C_yH_{2y+2-n}$, wherein y is an integer from 3 to 6;

$R^2$ is selected from the group consisting of alkyl radicals having 1 to 24 carbon atoms, aryl radicals having 6 to 12 carbon atoms and aralkyl radicals having 7 to 12 carbon atoms;

said process comprises reacting an alkyl thiopropionate of the structural formula:

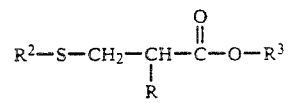

wherein $R^3$ is methyl or ethyl and $R^2$ and R are described above, with a glycol at temperatures between 50° C. and 180° C. in the presence of a catalytic amount of a dialkyl tin oxide.

2. A process according to claim 1 wherein the dialkyl tin oxide is dibutyl tin oxide.

3. A process according to claim 1 wherein the dialkyl tin oxide is present in an amount from 0.01 to 10% based on total weight of the reactants.

4. A process according to claim 1 wherein the dialkyl tin oxide is present in an amount from 0.05 to 2% based on total weight of the reactants.

5. A process according to claim 1 wherein the dialkyl tin oxide is present in an amount from 0.1 to 1% based on total weight of the reactants.

6. A process according to claim 1 wherein the glycol is tetraethylene glycol.

7. A process according to claim 1 wherein $R^2$ is an alkyl radical of 12 carbon atoms, R is a hydrogen or methyl radical and $R^3$ is a methyl radical.

8. A process according to claim 1 wherein the temperature is from 90°–145° C.

* * * * *